United States Patent
Auld et al.

(10) Patent No.: US 10,172,706 B2
(45) Date of Patent: Jan. 8, 2019

(54) INTRAOCULAR LENS INSERTER

(71) Applicant: NOVARTIS AG, Basel (CH)

(72) Inventors: Jack Robert Auld, Laguna Niguel, CA (US); John Christopher Huculak, Mission Viejo, CA (US); Matthew Douglas McCawley, San Clemente, CA (US); Matthew Braden Flowers, Aliso Viejo, CA (US); James Lescoulie, Lake Forest, CA (US)

(73) Assignee: Novartis AG, Basel (CH)

( * ) Notice: Subject to any disclaimer, the term of this patent is extended or adjusted under 35 U.S.C. 154(b) by 338 days.

(21) Appl. No.: 15/072,023

(22) Filed: Mar. 16, 2016

(65) Prior Publication Data

US 2017/0119522 A1    May 4, 2017

Related U.S. Application Data

(60) Provisional application No. 62/249,185, filed on Oct. 31, 2015.

(51) Int. Cl.
*A61F 2/16* (2006.01)
(52) U.S. Cl.
CPC ............ *A61F 2/1672* (2013.01); *A61F 2/167* (2013.01)
(58) Field of Classification Search
CPC ...... A61F 2/1662; A61F 2/1667; A61F 2/167; A61F 2/1672; A61F 2/1678
USPC ....................................................... 623/6.12
See application file for complete search history.

(56) References Cited

U.S. PATENT DOCUMENTS

| | | |
|---|---|---|
| 2,547,099 A | 4/1951 | Smoot |
| 4,429,421 A | 2/1984 | Levy |
| 4,573,998 A | 3/1986 | Mazzocco |
| 4,615,703 A | 10/1986 | Callahan et al. |
| 4,619,256 A | 10/1986 | Horn |
| 4,634,423 A | 1/1987 | Bailey et al. |
| 4,699,140 A | 10/1987 | Holmes et al. |
| 4,715,373 A | 12/1987 | Mazzocco et al. |
| 4,726,367 A | 2/1988 | Shoemaker |
| 4,747,404 A | 5/1988 | Jampel et al. |
| 4,763,650 A | 8/1988 | Hauser |
| 4,765,329 A | 8/1988 | Cumming et al. |
| 4,822,360 A | 4/1989 | Deacon |
| 4,844,065 A | 7/1989 | Faulkner |

(Continued)

FOREIGN PATENT DOCUMENTS

| | | |
|---|---|---|
| CA | 2858485 | 6/2013 |
| EP | 0174129 A1 | 3/1986 |

(Continued)

OTHER PUBLICATIONS

EP0477466, Dated Apr. 1, 1992, Adatomed Pharmazeutische, Abstract only.

(Continued)

*Primary Examiner* — Melanie Tyson

(57) ABSTRACT

Intraocular lens inserters and methods of use are disclosed. An example intraocular lens inserter may include an interior assembly having a movable member disposed therein. The movable member is movable in response to a pressure of a compressed gas. In response to the pressure of the compressed gas, the moveable member pressurizes a substantially incompressible fluid. The pressurized substantially incompressible fluid is used to advance a plunger. The plunger advances an intraocular lens through a lumen for insertion into an eye.

21 Claims, 11 Drawing Sheets

(56) References Cited

U.S. PATENT DOCUMENTS

| | | |
|---|---|---|
| 4,844,093 A | 7/1989 | Jampel et al. |
| 4,852,566 A | 8/1989 | Callahan et al. |
| 4,862,885 A | 9/1989 | Cumming |
| 4,880,000 A | 11/1989 | Holmes et al. |
| 4,906,247 A | 3/1990 | Fritch |
| 4,919,130 A | 4/1990 | Stoy et al. |
| 4,934,363 A | 6/1990 | Smith et al. |
| 5,007,913 A | 4/1991 | Dulebohn et al. |
| 5,064,413 A | 11/1991 | McKinnon et al. |
| 5,066,297 A | 11/1991 | Cumming |
| 5,098,439 A | 3/1992 | Hill et al. |
| 5,123,905 A | 6/1992 | Kelman |
| 5,190,552 A | 3/1993 | Kelman |
| 5,222,972 A | 6/1993 | Hill et al. |
| 5,304,182 A | 4/1994 | Rheinish et al. |
| 5,354,333 A | 10/1994 | Kammann et al. |
| 5,496,328 A | 3/1996 | Nakajima et al. |
| 5,562,676 A | 10/1996 | Brady et al. |
| 5,582,613 A | 12/1996 | Brady et al. |
| 5,582,614 A | 12/1996 | Feingold |
| 5,607,433 A | 3/1997 | Polla et al. |
| 5,616,148 A | 4/1997 | Eagles et al. |
| 5,629,577 A | 5/1997 | Polla et al. |
| 5,630,821 A | 5/1997 | Klaas |
| 5,643,275 A | 7/1997 | Blake |
| 5,643,276 A | 7/1997 | Zaleski |
| 5,693,057 A | 12/1997 | Dusek |
| 5,716,364 A | 2/1998 | Makker et al. |
| 5,772,666 A | 6/1998 | Feingold et al. |
| 5,772,667 A | 6/1998 | Blake |
| 5,776,138 A | 7/1998 | Vidal et al. |
| 5,800,441 A | 9/1998 | Polla et al. |
| 5,803,925 A | 9/1998 | Yang et al. |
| 5,807,400 A | 9/1998 | Chambers et al. |
| 5,810,833 A | 9/1998 | Brady et al. |
| 5,860,984 A | 1/1999 | Chambers et al. |
| 5,868,751 A | 2/1999 | Feingold |
| 5,873,879 A | 2/1999 | Figueroa et al. |
| 5,876,406 A | 3/1999 | Wolf et al. |
| 5,876,407 A | 3/1999 | Makker et al. |
| 5,876,440 A | 3/1999 | Feingold |
| 5,921,989 A | 7/1999 | Deacon et al. |
| 5,944,725 A | 8/1999 | Cicenas et al. |
| 5,947,975 A | 9/1999 | Kikuchi et al. |
| 5,947,976 A | 9/1999 | Van Noy et al. |
| 6,042,587 A | 3/2000 | Polla et al. |
| 6,162,230 A | 12/2000 | Polla et al. |
| 6,299,618 B1 | 10/2001 | Sugiura |
| 6,312,433 B1 | 11/2001 | Butts et al. |
| 6,334,862 B1 | 1/2002 | Vidal et al. |
| 6,336,932 B1 | 1/2002 | Figueroa et al. |
| 6,342,058 B1 | 1/2002 | Portney |
| 6,371,960 B2 | 4/2002 | Heyman |
| 6,387,101 B1 | 5/2002 | Butts et al. |
| 6,398,789 B1 | 6/2002 | Capetan |
| 6,428,545 B2 | 8/2002 | Portney |
| 6,468,282 B2 | 10/2002 | Kikuchi et al. |
| 6,491,697 B1 | 12/2002 | Clark |
| 6,500,181 B1 | 12/2002 | Portney |
| 6,500,239 B2 | 12/2002 | Castellano |
| 6,503,275 B1 | 1/2003 | Cumming |
| 6,506,195 B2 | 1/2003 | Chambers et al. |
| 6,537,281 B1 | 3/2003 | Portney |
| 6,537,283 B2 | 3/2003 | Van Noy |
| 6,540,754 B2 | 4/2003 | Brady |
| 6,554,839 B2 | 4/2003 | Brady |
| 6,558,395 B2 | 5/2003 | Hjertman et al. |
| 6,592,591 B2 | 7/2003 | Polla et al. |
| 6,607,537 B1 | 8/2003 | Binder |
| 6,629,979 B1 | 10/2003 | Feingold |
| 6,666,871 B2 | 12/2003 | Kikuchi et al. |
| 6,679,891 B2 | 1/2004 | Makker |
| 6,685,740 B2 | 2/2004 | Figueroa et al. |
| 6,712,848 B1 | 3/2004 | Wolf et al. |
| 6,723,104 B2 | 4/2004 | Ott |
| 6,733,507 B2 | 5/2004 | McNicholas |
| 6,858,033 B2 | 2/2005 | Kobayashi |
| 6,921,405 B2 | 7/2005 | Feingold |
| 6,923,815 B2 | 8/2005 | Brady |
| 6,976,989 B1 | 12/2005 | Vincent |
| 7,025,782 B2 | 4/2006 | Kobayashi et al. |
| 7,033,366 B2 | 4/2006 | Brady |
| 7,037,312 B2 | 5/2006 | Kikuchi et al. |
| 7,037,328 B2 | 5/2006 | Vincent |
| 7,131,976 B2 | 11/2006 | Kobayashi |
| 7,137,994 B2 | 11/2006 | De Juan, Jr. |
| 7,156,854 B2 | 1/2007 | Brown et al. |
| 7,156,855 B2 | 1/2007 | Oda |
| 7,276,071 B2 | 10/2007 | Lin |
| 7,279,006 B2 | 10/2007 | Vincent |
| 7,335,209 B2 | 2/2008 | Meyer |
| RE40,185 E | 3/2008 | Kikuchi et al. |
| 7,348,038 B2 | 3/2008 | Makker |
| 7,422,604 B2 | 9/2008 | Vaquero et al. |
| 7,429,263 B2 | 9/2008 | Vaquero et al. |
| 7,458,976 B2 | 12/2008 | Peterson |
| 7,476,229 B2 | 1/2009 | Meyer |
| 7,476,230 B2 | 1/2009 | Ohno et al. |
| 7,645,300 B2 | 1/2010 | Tsai |
| 7,687,097 B2 | 3/2010 | Makker |
| 7,704,258 B2 | 4/2010 | Feingold |
| 7,717,879 B2 | 5/2010 | Mansouri |
| 7,740,607 B2 | 6/2010 | Willis et al. |
| 7,740,636 B2 | 6/2010 | Lee |
| 7,744,603 B2 | 6/2010 | Zadno Azizi |
| 7,867,240 B2 | 1/2011 | Peterson |
| 7,892,283 B2 | 2/2011 | Shepherd |
| 7,901,414 B2 | 3/2011 | Tourrette |
| 7,947,049 B2 | 5/2011 | Vaquero |
| 7,988,701 B2 | 8/2011 | Vaquero et al. |
| 8,021,423 B2 | 9/2011 | Tanaka |
| 8,048,085 B2 | 11/2011 | Peterson |
| 8,062,360 B2 | 11/2011 | Pollock |
| 8,080,017 B2 | 12/2011 | Tanaka |
| 8,114,095 B2 | 2/2012 | Rathert |
| 8,123,719 B2 | 2/2012 | Edwards |
| 8,123,804 B2 | 2/2012 | Tanaka |
| 8,142,498 B2 | 3/2012 | Tsai |
| 8,152,817 B2 | 4/2012 | Tanaka |
| 8,216,629 B2 | 7/2012 | Mentak |
| 8,225,643 B2 | 7/2012 | Abboud et al. |
| 8,246,631 B2 | 8/2012 | Pynson |
| 8,252,053 B2 | 8/2012 | Pynson |
| 8,308,736 B2 | 11/2012 | Boukhny et al. |
| 8,308,799 B2 | 11/2012 | Chen |
| 8,500,681 B2 | 8/2013 | Gonnelli |
| 8,574,196 B2 | 11/2013 | Stammen et al. |
| 8,579,969 B2 | 11/2013 | Zacharias |
| 8,617,099 B2 | 12/2013 | Williamson |
| 8,657,835 B2 | 2/2014 | Boukhny et al. |
| 8,668,734 B2 | 3/2014 | Hildebrand et al. |
| 8,721,702 B2 | 5/2014 | Ramada et al. |
| 8,758,433 B2 | 6/2014 | Cole et al. |
| 8,956,408 B2 | 2/2015 | Smiley et al. |
| 8,968,396 B2 | 3/2015 | Matthews et al. |
| 8,998,983 B2 | 4/2015 | Auld |
| 9,228,273 B2 | 1/2016 | Keszler et al. |
| 9,255,665 B2 | 2/2016 | Brouillette et al. |
| 2001/0007075 A1 | 7/2001 | Hjertman et al. |
| 2001/0007942 A1 | 7/2001 | Kikuchi et al. |
| 2001/0015593 A1 | 8/2001 | Polla et al. |
| 2002/0193803 A1 | 12/2002 | Portney |
| 2003/0187455 A1 | 10/2003 | Kobayashi et al. |
| 2003/0212406 A1 | 11/2003 | Kobayashi et al. |
| 2003/0212407 A1 | 11/2003 | Kikuchi et al. |
| 2003/0216745 A1 | 11/2003 | Brady et al. |
| 2004/0059343 A1 | 3/2004 | Shearer et al. |
| 2004/0127911 A1 | 7/2004 | Figueroa et al. |
| 2004/0215207 A1 | 10/2004 | Cumming |
| 2004/0267359 A1 | 12/2004 | Makker |
| 2005/0033308 A1 | 2/2005 | Callahan |
| 2005/0171555 A1 | 8/2005 | Tran et al. |
| 2005/0222577 A1 | 10/2005 | Vaquero |
| 2005/0267403 A1 | 12/2005 | Landau et al. |

(56) References Cited

U.S. PATENT DOCUMENTS

| | | |
|---|---|---|
| 2005/0283162 A1 | 12/2005 | Stratas |
| 2005/0283163 A1 | 12/2005 | Portney |
| 2005/0283164 A1 | 12/2005 | Wu et al. |
| 2006/0085013 A1 | 4/2006 | Dusek |
| 2006/0129125 A1 | 6/2006 | Copa et al. |
| 2006/0142780 A1 | 6/2006 | Pynson et al. |
| 2006/0142781 A1 | 6/2006 | Pynson et al. |
| 2006/0167466 A1 | 7/2006 | Dusek |
| 2006/0184181 A1 | 8/2006 | Cole |
| 2006/0264971 A1 | 11/2006 | Akahoshi |
| 2006/0271063 A1 | 11/2006 | Sunada et al. |
| 2006/0287655 A1 | 12/2006 | Khuray et al. |
| 2006/0293694 A1 | 12/2006 | Futamura |
| 2007/0060925 A1 | 3/2007 | Pynson |
| 2007/0112355 A1 | 5/2007 | Salahieh et al. |
| 2007/0203502 A1 | 8/2007 | Makker |
| 2007/0270881 A1 | 11/2007 | Hishinuma et al. |
| 2007/0270945 A1 | 11/2007 | Kobayashi |
| 2008/0004610 A1 | 1/2008 | Miller et al. |
| 2008/0027460 A1 | 1/2008 | Kobayashi |
| 2008/0027461 A1 | 1/2008 | Vaquero et al. |
| 2008/0033449 A1 | 2/2008 | Cole et al. |
| 2008/0039862 A1 | 2/2008 | Tran |
| 2008/0058830 A1 | 3/2008 | Cole et al. |
| 2008/0086146 A1 | 4/2008 | Ishii |
| 2008/0097459 A1 | 4/2008 | Kammerlander |
| 2008/0097460 A1 | 4/2008 | Boukhny et al. |
| 2008/0097461 A1 | 4/2008 | Boukhny et al. |
| 2008/0114203 A1 | 5/2008 | Crank |
| 2008/0119783 A1 | 5/2008 | Green |
| 2008/0147080 A1 | 6/2008 | Pynson |
| 2008/0147081 A1 | 6/2008 | Pynson |
| 2008/0147082 A1 | 6/2008 | Pynson |
| 2008/0154361 A1 | 6/2008 | Pynson et al. |
| 2008/0171968 A1 | 7/2008 | Stout |
| 2008/0208176 A1 | 8/2008 | Loh |
| 2008/0255579 A1 | 10/2008 | Wollenhaupt |
| 2008/0269770 A1 | 10/2008 | Pynson et al. |
| 2009/0005788 A1 | 1/2009 | Rathert |
| 2009/0018548 A1 | 1/2009 | Charles |
| 2009/0024136 A1 | 1/2009 | Martin et al. |
| 2009/0030425 A1 | 1/2009 | Smiley et al. |
| 2009/0036898 A1 | 2/2009 | Ichinohe et al. |
| 2009/0043313 A1 | 2/2009 | Ichinohe et al. |
| 2009/0112222 A1 | 4/2009 | Barrows |
| 2009/0198247 A1 | 8/2009 | Ben Nun |
| 2009/0204122 A1 | 8/2009 | Ichinohe et al. |
| 2009/0234366 A1 | 9/2009 | Tsai et al. |
| 2009/0248031 A1 | 10/2009 | Ichinohe et al. |
| 2009/0270876 A1 | 10/2009 | Hoffmann et al. |
| 2009/0292293 A1 | 11/2009 | Bogaert et al. |
| 2009/0318933 A1 | 12/2009 | Anderson |
| 2010/0010498 A1 | 1/2010 | Biddle et al. |
| 2010/0057095 A1 | 3/2010 | Khuray et al. |
| 2010/0076450 A1 | 3/2010 | Yoshida |
| 2010/0082037 A1 | 4/2010 | Kobayashi et al. |
| 2010/0087832 A1 | 4/2010 | Seyboth |
| 2010/0094309 A1 | 4/2010 | Boukhny et al. |
| 2010/0106160 A1 | 4/2010 | Tsai |
| 2010/0121340 A1 | 5/2010 | Downer |
| 2010/0125278 A1 | 5/2010 | Wagner |
| 2010/0125279 A1 | 5/2010 | Karakelle |
| 2010/0160926 A1 | 6/2010 | Artsyukhovich |
| 2010/0161049 A1 | 6/2010 | Inoue |
| 2010/0185206 A1 | 7/2010 | Ichinohe et al. |
| 2010/0204704 A1 | 8/2010 | Davies et al. |
| 2010/0204705 A1 | 8/2010 | Brown et al. |
| 2010/0217273 A1 | 8/2010 | Someya et al. |
| 2010/0217274 A1 | 8/2010 | Lee et al. |
| 2010/0228260 A1 | 9/2010 | Callahan et al. |
| 2010/0228261 A1 | 9/2010 | Feingold et al. |
| 2010/0256651 A1 | 10/2010 | Jani et al. |
| 2010/0280521 A1 | 11/2010 | Vaquero et al. |
| 2010/0286704 A1 | 11/2010 | Ichinohe et al. |
| 2010/0305577 A1 | 12/2010 | Muchhala |
| 2010/0312254 A1 | 12/2010 | Downer et al. |
| 2011/0046633 A1 | 2/2011 | Pankin |
| 2011/0046634 A1 | 2/2011 | Rathert |
| 2011/0046635 A1 | 2/2011 | Pankin |
| 2011/0082463 A1 | 4/2011 | Inoue |
| 2011/0098717 A1 | 4/2011 | Inoue |
| 2011/0144653 A1 | 6/2011 | Pankin |
| 2011/0152872 A1 | 6/2011 | Seyboth et al. |
| 2011/0152873 A1 | 6/2011 | Shepherd |
| 2011/0172676 A1 | 7/2011 | Chen |
| 2011/0190777 A1 | 8/2011 | Hohl |
| 2011/0213380 A1 | 9/2011 | Han |
| 2011/0224677 A1 | 9/2011 | Niwa et al. |
| 2011/0245840 A1 | 10/2011 | Seyboth et al. |
| 2011/0264101 A1 | 10/2011 | Inoue |
| 2011/0264102 A1 | 10/2011 | Cole et al. |
| 2011/0264103 A1 | 10/2011 | Cole et al. |
| 2011/0270264 A1 | 11/2011 | Shoji et al. |
| 2011/0288557 A1 | 11/2011 | Kudo et al. |
| 2011/0295264 A1 | 12/2011 | Cole et al. |
| 2011/0313425 A1 | 12/2011 | Han |
| 2012/0016374 A1 | 1/2012 | Han |
| 2012/0016375 A1 | 1/2012 | Peterson |
| 2012/0022547 A1 | 1/2012 | Hilderbrand et al. |
| 2012/0022548 A1 | 1/2012 | Zacharias |
| 2012/0071888 A1 | 3/2012 | Putallaz et al. |
| 2012/0130390 A1 | 5/2012 | Davies |
| 2012/0158007 A1 | 6/2012 | Brown et al. |
| 2012/0165824 A1 | 6/2012 | Tsai |
| 2012/0245591 A1 | 9/2012 | Matthews |
| 2012/0253356 A1 | 10/2012 | Niwa et al. |
| 2012/0289969 A1 | 11/2012 | Seyboth et al. |
| 2012/0289970 A1 | 11/2012 | Pynson |
| 2012/0296264 A1 | 11/2012 | Boukhny et al. |
| 2013/0012956 A1 | 1/2013 | Mirlay |
| 2013/0035939 A1 | 2/2013 | Gilbert |
| 2013/0041382 A1 | 2/2013 | Ben Nun |
| 2013/0197531 A1 | 8/2013 | Boukhny et al. |
| 2013/0197532 A1 | 8/2013 | Boukhny et al. |
| 2013/0281927 A1 | 10/2013 | Jennings et al. |
| 2014/0200590 A1 | 7/2014 | Chen |
| 2015/0088149 A1 | 3/2015 | Auld |
| 2015/0282928 A1 | 10/2015 | Auld et al. |
| 2015/0342726 A1 | 12/2015 | Deacon et al. |
| 2016/0015511 A1 | 1/2016 | Auld et al. |

FOREIGN PATENT DOCUMENTS

| | | |
|---|---|---|
| EP | 0477466 A1 | 4/1992 |
| EP | 0937466 A2 | 8/1999 |
| EP | 1175187 A1 | 1/2002 |
| EP | 1344503 A1 | 9/2003 |
| EP | 1481652 A1 | 12/2004 |
| EP | 1144031 B1 | 10/2005 |
| EP | 1736118 A1 | 12/2006 |
| EP | 1857075 A1 | 11/2007 |
| EP | 2074962 A1 | 7/2009 |
| EP | 2324797 A2 | 5/2011 |
| EP | 2368526 A1 | 9/2011 |
| EP | 2491902 B1 | 8/2012 |
| EP | 2502603 B1 | 9/2012 |
| EP | 1539065 B1 | 12/2012 |
| EP | 1748811 B1 | 12/2012 |
| EP | 2178464 B1 | 8/2013 |
| EP | 2560578 B1 | 6/2016 |
| EP | 3075353 A1 | 10/2016 |
| EP | 3122286 | 2/2017 |
| JP | 3207374 | 9/1991 |
| JP | 2004261263 | 9/2004 |
| JP | 2007215990 | 8/2007 |
| JP | 2008500876 | 1/2008 |
| JP | 2016049321 A2 | 4/2016 |
| RU | 2386423 C2 | 4/2010 |
| WO | 199637152 A1 | 11/1996 |
| WO | 200164147 A1 | 9/2001 |
| WO | 2007098622 A1 | 9/2007 |
| WO | 2007112130 A2 | 10/2007 |
| WO | 2010028873 A1 | 3/2010 |
| WO | 2011133823 A1 | 10/2011 |

(56) References Cited

FOREIGN PATENT DOCUMENTS

| WO | 2012006616 A2 | 1/2012 |
| WO | 12086797 A1 | 6/2012 |
| WO | 13076067 A1 | 5/2013 |
| WO | 2013086612 A1 | 6/2013 |
| WO | 2015154049 | 12/2013 |
| WO | 2013184727 A1 | 2/2014 |
| WO | 2014149459 A1 | 9/2014 |
| WO | 15144890 A1 | 10/2015 |
| WO | 2015144870 A1 | 10/2015 |
| WO | 2015144890 A1 | 10/2015 |
| WO | 2015154049 A1 | 10/2015 |
| WO | 2014089250 A1 | 6/2016 |
| WO | 2016208725 A1 | 12/2016 |
| WO | 17047715 A1 | 3/2017 |

OTHER PUBLICATIONS

RU2386423 with English translation.
2016049321 JP Abstract translation only.
WO2012086797 Abstract translation only.
WO2017047715 Abstract translation only.

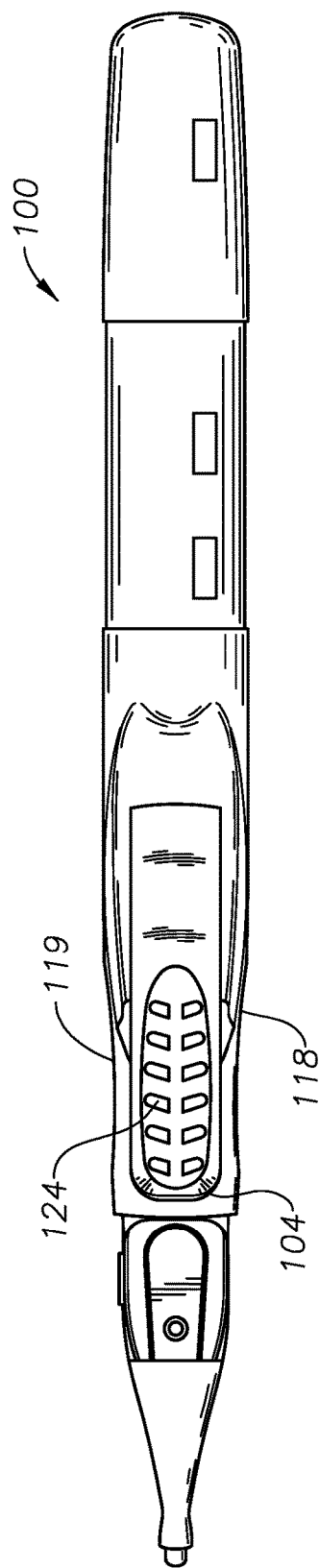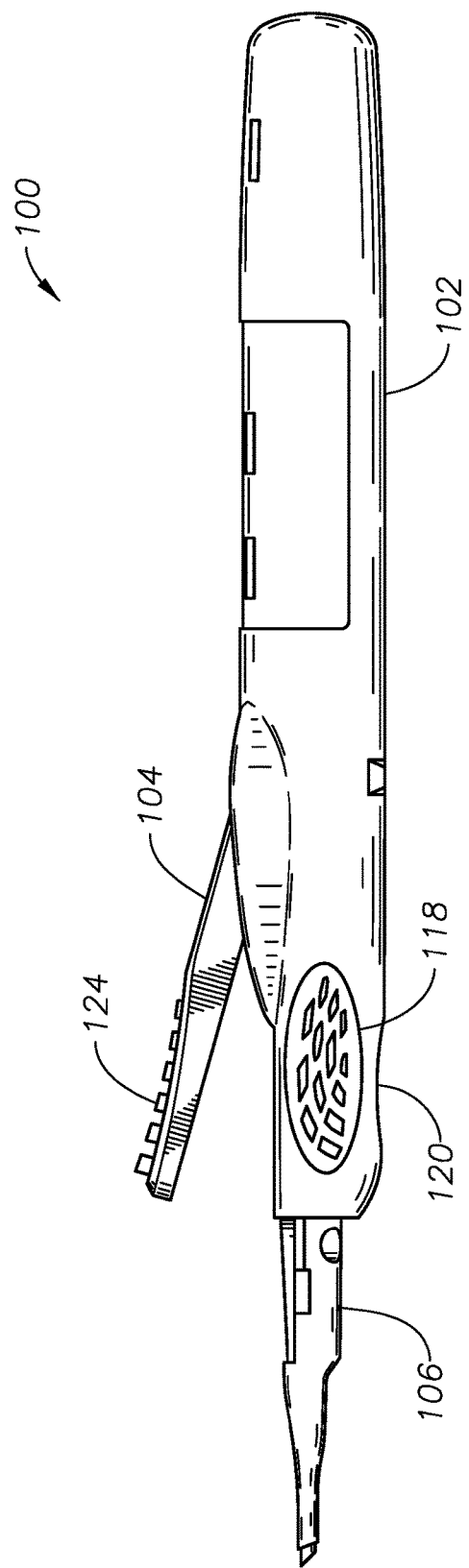

INTRAOCULAR LENS INSERTER

CROSS-REFERENCE TO RELATED APPLICATION

This application claims the benefit of U.S. Provisional Application No. 62/249,185, filed Oct. 31, 2015, the entire contents of which are incorporated herein by reference.

TECHNICAL FIELD

The present disclosure relates to systems, devices, and methods for inserting an intraocular lens into an eye and, particularly, to utilizing a compressed fluid to insert an intraocular lens into an eye.

SUMMARY

A first aspect of the present disclosure may include an intraocular lens inserter having an inserter body defining a first interior cavity, a compressed gas container coupled to the inserter body, an assembly disposed within the cavity and moveable within the first interior cavity relative to the inserter body, and a plunger. The assembly may include a housing, a second interior cavity formed within the housing, and a moveable member disposed within the second interior cavity and moveable therein relative to the housing. The moveable member may divide the second interior cavity into a first portion adapted to receive a compressed gas from the compressed gas container and a second portion configured to contain a substantially incompressible fluid. The moveable member may be configured to impart a pressure from the pressurized gas to the substantially incompressible fluid contained. The plunger may be movable in response to pressure imparted by the substantially incompressible fluid.

According to another aspect, the disclosure describes an intraocular lens inserter that may include an inserter body defining a first interior cavity, a pressurized gas canister disposed in the first interior cavity, an assembly disposed in the first interior cavity and moveable therein relative to the inserter body, and an actuator pivotably coupled to the inserter body. The assembly may include a first housing defining a second interior cavity, a valve body disposed at a first end of the first housing, a moveable member disposed in the second interior cavity and movable relative to the first housing, and a piercing member disposed at a second end of the first housing that is opposite the first end. The actuator may include a lever arm that engages the assembly. The actuator may be operable to displace the assembly within the inserter body when the actuator is pivoted relative to the inserter body.

The various aspects may include one or more of the following features. An actuator may be moveable between an unactuated position and an actuated position. The actuator may be operable to displace the interior assembly between an initial position and a displaced position relative to the compressed gas canister in response to movement of the actuator to the actuated position. A resilient member may be disposed between the housing and the compressed gas canister. The resilient member may be configured to apply a biasing force that urges the assembly towards the initial position when the actuator is moved into the actuated position. The assembly may include a piercing member configured to pierce the compressed gas container. The piercing member may be configured to pierce the compressed gas container in response to displacement of the assembly relative to the gas canister. The intraocular lens inserter may include an orifice, and the assembly may include a valve body. The valve body may include an aperture and a needle valve receivable into the orifice. Displacement of assembly within the inserter body may displace the needle valve relative to the orifice to provide in fluid communication between the second portion of the second interior cavity and the orifice via the aperture.

The various aspects may also include one or more of the following features. a plunger housing may also be included. The plunger housing may form a third interior cavity configured to receive the plunger. The third interior cavity may be in fluid communication with the orifice, and the substantially incompressible fluid may flow through the aperture and the orifice to apply pressure to the plunger to displace the plunger within the third interior cavity in response to displacement of the assembly within the inserter body. The needle valve may include a tapered surface, and displacement of the needle valve within the orifice may form a gap between the tapered surface of the needle valve and the orifice that varies with an amount by which the needle valve is moved relative to the orifice.

The various aspects may further include one or more of the following features. The piercing member may be configured to pierce the pressurized gas canister when the assembly is displaced within the inserter body. The assembly may include a passage operable to communicate compressed gas released from the compressed gas canister into the second interior cavity. The moveable member may be displaceable within the second interior cavity in response to pressurized gas released from the pressurized gas canister. The moveable member may divide the interior cavity into a first portion and a second portion, and a substantially incompressible fluid may be disposed in the second portion. The assembly may include a passage between the first portion and the compressed gas canister, and wherein compressed gas released from the compressed gas canister may be communicated to the first portion via the passageway.

The various aspects may include one or more of the following features. An intraocular lens inserter may also include a plunger housing, a plunger received into a chamber formed in the plunger housing, and an orifice formed in the plunger housing. The orifice may be in fluid communication with the chamber formed in the plunger housing. The valve body may include a needle valve removably received into the orifice. The needle valve may be displaceable from the orifice in response to a displacement of the assembly within the inserter body. Displacement of the needle valve from the orifice may provide fluid communication between a substantially incompressible fluid contained within the second portion of the second interior cavity and the chamber formed in the plunger housing. The assembly may be moveable between a first position in which the needle valve is seated within the orifice and a second position in which the needle valve is unseated from the orifice and the piercing member penetrates the gas canister to release the compressed gas into the first portion in response to articulation of the actuator from a third position to a fourth position. The movable member may be displaceable within the second interior cavity and operable to transmit the pressure of the compressed gas within the first portion to the substantially incompressible fluid contained in the second portion in response to the pressure of the compressed gas. The substantially incompressible fluid may be flowable into the chamber via the orifice in response to displacement of the moveable member, and the plunger may be movable within the chamber in response to pressure transmitted thereto by the substantially incompressible fluid. A biasing member may be disposed between the assembly and the compressed gas canister. The biasing member may apply a biasing force when the assembly is displaced from the first position that urges the assembly back into the first position. The needle valve may include a tapered surface, and a gap may be formed between the tapered surface of the needle valve and the orifice when the needle valve is unseated from the orifice. A size of the gap may be altered by the amount by which the needle valve is displaced relative to the orifice. The size of the gap may be altered in response to an amount by which the actuator is pivoted relative to the inserter body.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

FIG. 2 shows a top vie of the example intraocular lens inserter of FIG. 1.

FIG. 3 shows a side view of the example intraocular lens inserter shown in FIG. 1.

DETAILED DESCRIPTION

Figure 1:
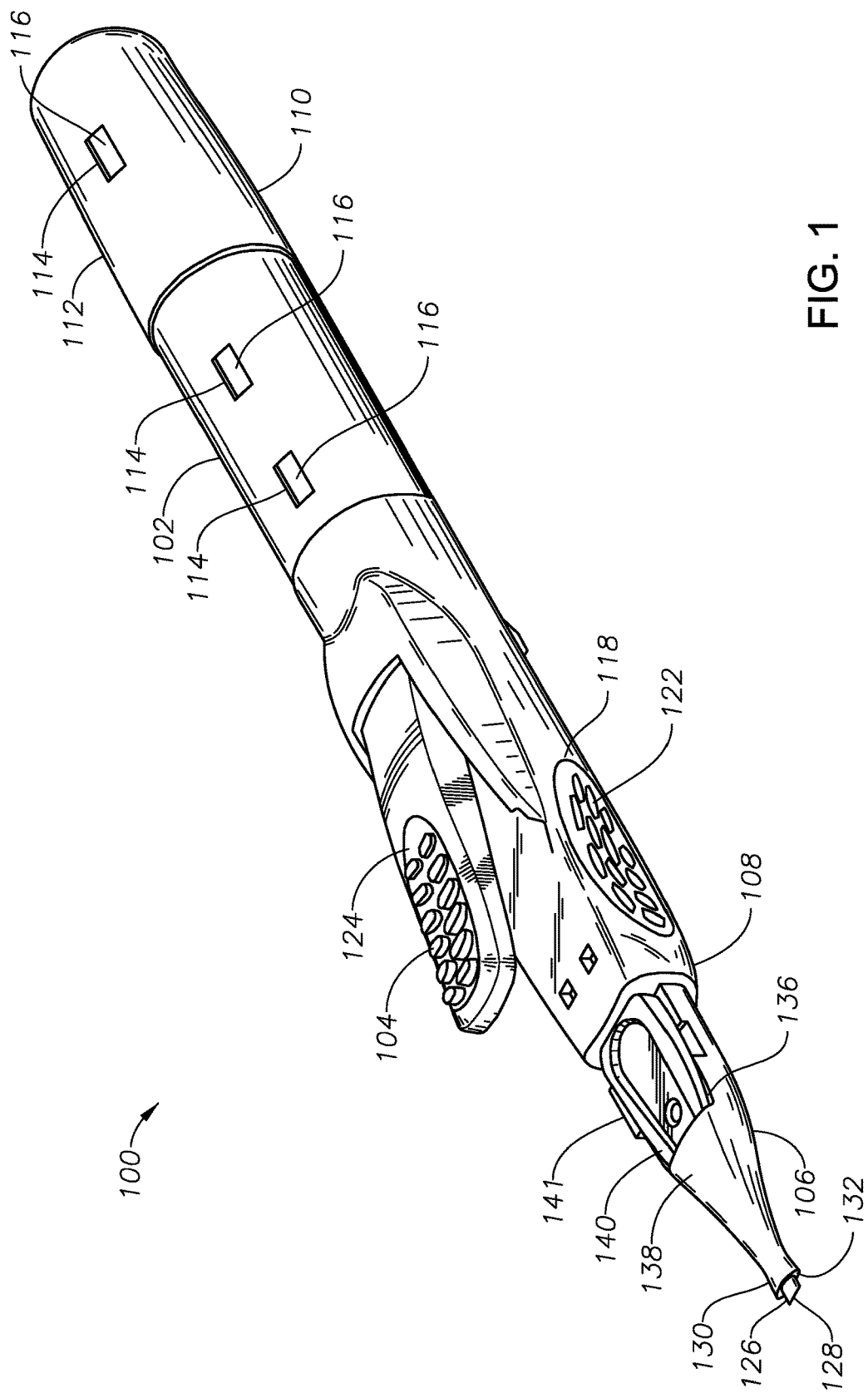
FIG. 1 is an example intraocular lens inserter.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

The present disclosure relates to systems, methods, and devices for inserting an intraocular lens ("IOL") into an eye. Particularly, the present disclosure describes methods, devices, and systems that utilize a compressed fluid to insert an intraocular lens into an eye.

FIG. 1 shows a perspective view of an example IOL inserter 100 having a body 102, a lever 104 that is pivotably coupled to the body 102, and a nozzle 106 connected to a distal end 108 of the body 102. The body 102 defines a cavity 103, as shown in greater detail below in relation to FIG. 4. In some instances, the nozzle 106 may be integrally connected to the body 102. In other instances, the nozzle 106 may be separate from the body 102 and may be coupled to the body 102 via an interlocking relationship. In some instances, the body 102 may have a slender, elongated shape. In some instances, the body 102 may have a first half 110 and a second half 112. The first half 110 may include a plurality of apertures 114. The second half 112 may include a plurality of tabs 116 that are received into the apertures 114 to join the first half 110 and the second half 112. The tabs 116 may form an interlocking fit with the apertures 114. However, the construction of the body 102 is not so limited. Rather, in some instances, the body 102 may be a single unitary piece. In some instances, the body 102 may include one or more cylindrical pieces. Moreover, the body 102 may be constructed in any desirable manner from any number of components.

Referring to FIGS. 1-3, the body 102 may also include reliefs 118, 119, and 120. The reliefs 118, 119, and 120 are shallow recesses formed in the body to accommodate, for example, one or more fingers of a user. One or more of the reliefs 118, 119, and 120 may include a textured surface 122 that may provide a user with an improved grip of and control over the IOL inserter 100. As shown in FIGS. 1-2, the reliefs 118 and 119 include texture surfaces 122. However, the scope is not so limited. Rather any, all, or none of the reliefs 118, 119, and 120 may include a textured surface. Similarly, the lever 104 is shown as including a textured surface 124. However, in some instances, the lever 104 may not include a textured surface.

Figure 4:
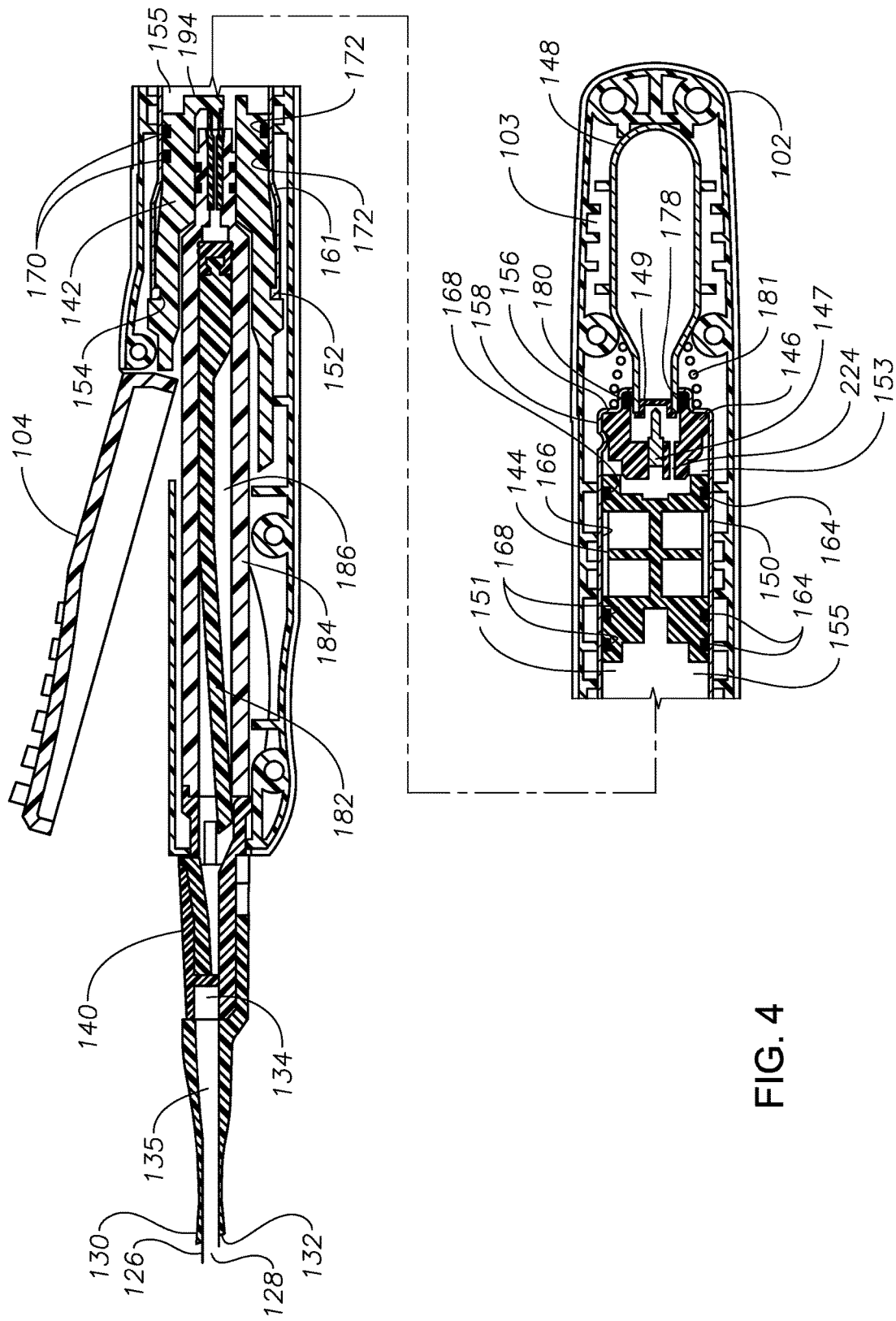
FIG. 4 is a cross-sectional view of the example intraocular lens inserter shown in FIG. 1.

The nozzle 106 includes a distal tip 126 that defines an opening 128, shown in greater detail in FIG. 4. The nozzle 106 may also include a flared portion or wound guard 130. The distal tip 118 is adapted to be inserted into a wound formed in an eye in order to deliver an IOL thereinto. The wound guard 130 includes an end surface 132 that is operable to contact an exterior surface of an eye in order to limit the depth to which the distal tip 118 may penetrate the eye. In some instance, though, the wound guard 130 may be omitted.

In some implementations, the IOL inserter 100 may be preloaded. That is, when provided to an end-user, the IOL inserter 100 may have an IOL already present therewithin and ready to deliver. Having the IOL inserter 100 preloaded with an IOL reduces the number of steps a user is required to accomplish before delivering the IOL into a patient. With a reduced number of steps, error and risk associated with delivery of an IOL into a patient may be reduced. Further, an amount of time required to deliver an IOL may also be reduced.

Referring to FIGS. 1 and 4, the nozzle 106 includes a chamber 134 into which an IOL in received. A lumen 135 extends from the chamber 134 to the opening 128. The lumen 135 is configured to fold an IOL as the IOL passes through the lumen 135. The IOL may be inserted into the chamber 134 via an opening 136 formed in a first side 138 of the nozzle 106. The opening 136 may be enclosed by a door 140. In some instances, the door 140 may be pivotably connected to the nozzle 106 via a hinge 141. In some instances, the door 140 may be integrally formed with the nozzle 106. In other instances, the door 140 may be fully removable from the nozzle 106.

Figure 5A:
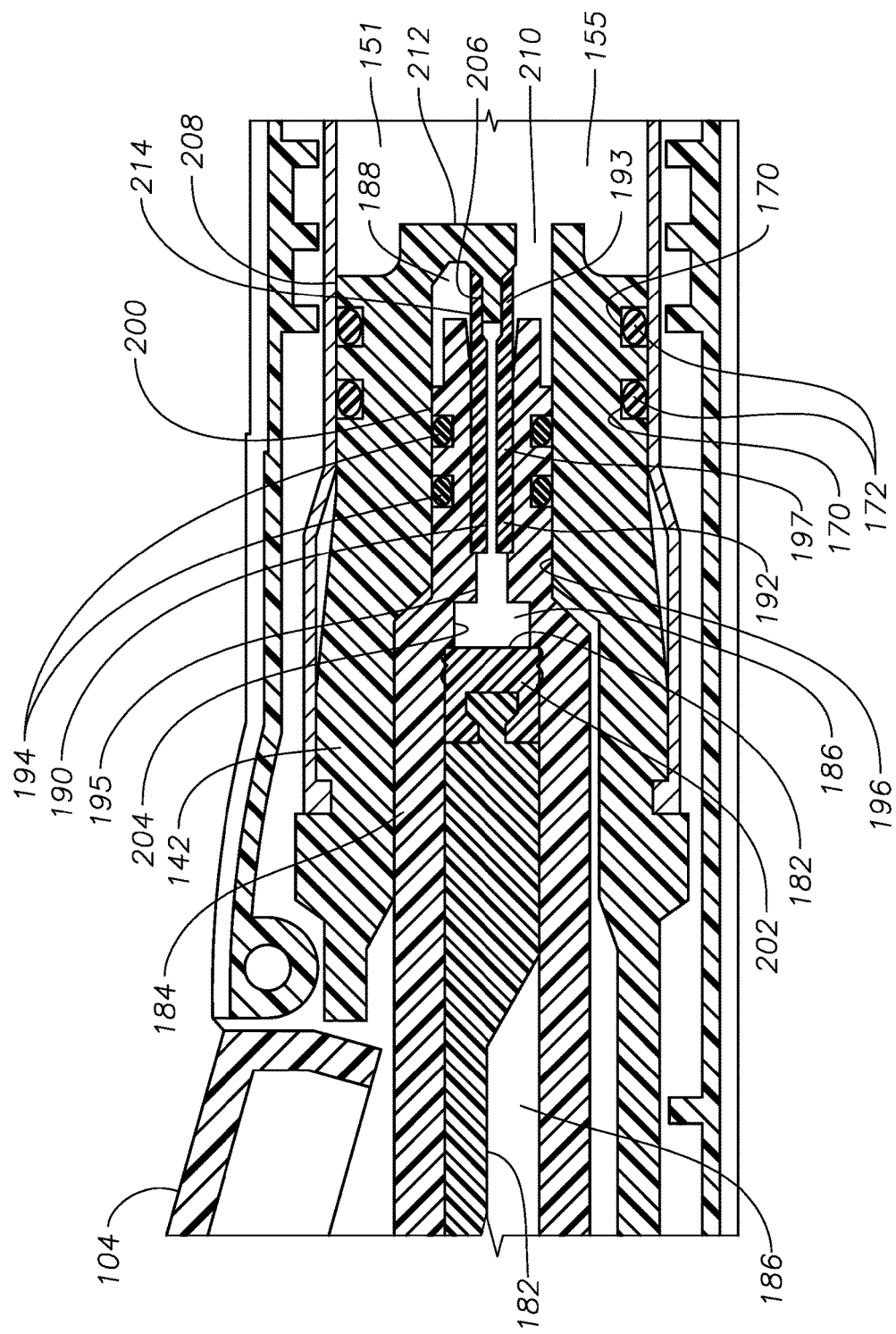
FIG. 5A is a partial cross-sectional view of an example intraocular lens inserter that includes a valve body, an interior assembly of the example intraocular lens inserter being in an initial, unarticulated position.
Figure 5B:
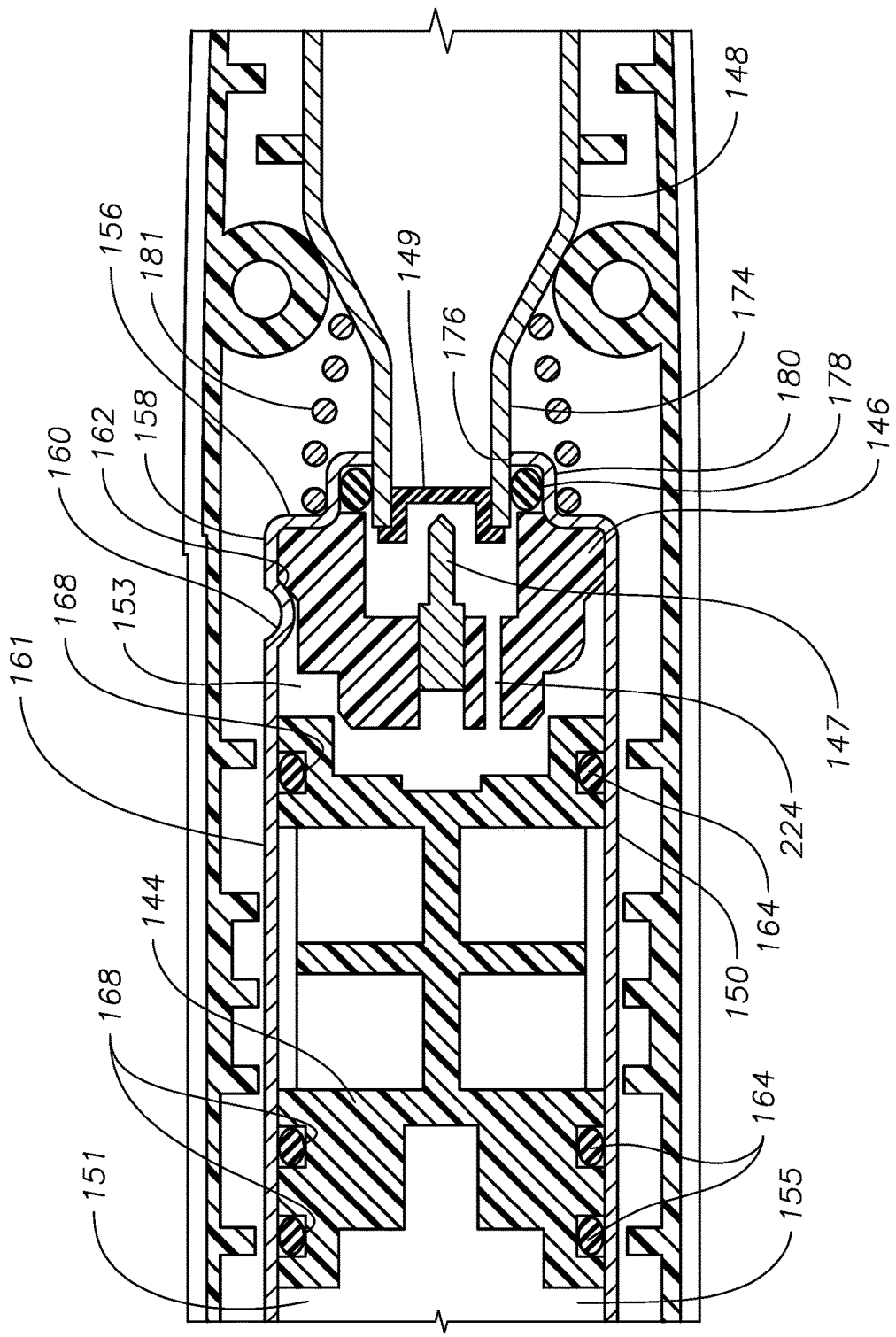
FIG. 5B also shows a partial cross-sectional view of an example intraocular lens inserter that includes a bulkhead, an interior assembly of the example intraocular lens inserter being in an initial, unarticulated position.

Referring to FIGS. 4, 5A, and 5B, the IOL inserter 100 includes a valve body 142, a moveable member or piston 144, a bulkhead 146, a canister 148, and an inner housing 150. The inner housing 150 defines a cavity 151. At least a portion of the valve body 142, the piston 144, and the bulkhead 146 may be disposed within the cavity 151 of the inner housing 150. Further, the valve body 142 and the bulkhead 146 may be fixedly attached to the inner housing 150. For example, the inner housing 150 may include tabs 152 that are received into an annular recess 154 formed in the valve body 142. A proximal end 156 of the inner housing 150 may be contoured to conform to the proximal end 158 of the bulkhead 146, and the inner housing 150 may include a protruding portion 160 that engages a lip 162 formed on the bulkhead 146, securing the bulkhead 146 relative to the inner housing 150 to maintain a position of the bulkhead relative to the inner housing 150. However, the valve body 142 and the bulkhead 146 may be fixedly coupled to the inner housing 150 in any desired or suitable manner. As a consequence, the inner housing 150, the valve body 142, the piston 144, and the bulkhead 146 define an assembly 161 and are moveable together within the body 102.

The bulkhead 146 includes a piercing member 147, such as a puncture pin, and the canister 148 may include a lid 149. The canister 148 confines a compressed gas. In some instances, the canister 148 confines carbon dioxide ($CO_2$). In some instances, the $CO_2$ within the canister 148 is in liquid form. In still other instances, the $CO_2$ within the canister 148 may be in a two-phase form. That is, a portion of the $CO_2$ within the canister may be in a gaseous form while another portion of the $CO_2$ may be in a liquid form. As explained in more detail below, the piercing member 147 is adapted to pierce the lid 149. Upon puncture of the lid 149, the $CO_2$ escapes the canister 148 in the form of gaseous $CO_2$. However, a portion of the $CO_2$ remaining within the canister 148 may remain in liquid form. The portion of $CO_2$ remaining in liquid form provides for a constant gas pressure released into the cavity 151. The $CO_2$ remaining in liquid form operates to provide a constant gas force as the IOL inserter 100 operates to fold and deliver an IOL. As discussed in more detail below, upon puncture of the lid 149, the gaseous $CO_2$ escapes the canister 148 and displaces the piston 144. Displacement of the piston increases a volume occupied by the gaseous $CO_2$. However, because liquid $CO_2$ is present, the gas pressure is not diminished notwithstanding the increase in volume. Rather, a portion of the liquid $CO_2$ changes phases forming a gas so that the $CO_2$ gas pressure remains constant. In some implementations, the amount of liquid $CO_2$ remaining is selected so that the gas pressure and, hence, driving force of the IOL inserter 100 remains constant throughout the entire stroke of plunger 182. In other words, the amount of $CO_2$ may be selected so that the force applied to engage, fold, and expel an IOL out of the IOL inserter remains constant.

While $CO_2$ may be used in some implementations, any gas may be used. Still further, in some instances, the canister 148 may not include a lid, and the piercing member 147 may puncture the canister 148 at any desired or suitable location.

The piston 144 is slideable within the cavity 151 and relative to the inner housing 150. The piston 144 divides the cavity 151 into a first portion 153 and a second portion 155. The piston 144 may include a seals 164 that engage an inner surface 166 of the inner housing 150. The seals 164 are adapted to provide a fluid-tight or substantially fluid-tight seal between the inner housing 150 and the piston 144. In some implementations, the each of the seals 164 may be disposed in corresponding annular grooves 168 formed in the piston 144. In some instances, the seals 164 may be O-rings. However, the seals 164 may be any desired or suitable material or device operable to provide a fluid-tight or substantially-fluid tight seal between the inner housing 150 and the piston 144. Further, in some instances, the seals 164 may be coupled to the piston 144 in any desired or suitable manner. For example, the seals 164 may be bonded to the piston 146, such as with an adhesive, ultrasonic weld, or any other type of bonding manner.

The valve body 142 may also include seals 170 that engage the inner surface 166 of the inner housing 150. The seals 170 may be similar to the seals 164. For example, the seals 170 may be O-rings disposed in the annular groove 172. However, in other instances, the seals 170 may be any desired or suitable sealing material attached or fitted to the valve body 142 in any desired or suitable manner.

The canister 148 may have a fixed position relative to the housing 102. The canister 148 may include a neck portion 174 that is received into an opening 176 formed in the proximal end 156 of the inner housing 150. A seal 178 is disposed circumferentially between a portion of the neck portion 174 and inner surface 166 of the inner housing 150. In some instances, the seal 178 may be an O-ring. Further, the seal 178 may be contained within a compartment 180 formed at the proximal end 156 of the inner housing 150. The seal 178 is adapted to provide a fluid-tight or substantially fluid-tight seal between the inner housing 150 and the canister 148. As also shown in FIG. 4, a biasing member 181 may be disposed between canister 148 and the inner housing 150. In some instances, the biasing member 181 may be a spring. Particularly, in some instances, the biasing member 181 may be a coil spring, a tapered coil spring, or any other type of device operable to apply a biasing force.

Referring to FIGS. 5A, 5B, 6A, and 6B, the IOL inserter 100 may also include a plunger 182 and a plunger housing 184. FIG. 5 illustrates a portion of the IOL inserter 100 with the assembly 161 in an initial, unactuated position. In this position, the needle valve 206 is seated within an orifice 190, particularly an enlarged portion 193 of the orifice 190. The orifice 190 also includes a reduced portion 197. The reduced portion 197 may extend distally from the enlarged portion 193. FIG. 6 illustrates the portion of the IOL inserter 100 shown in FIG. 5 with the assembly 161 in an articulated position. In the articulated position, the piercing member 147 has pierced and extends into the canister 148 and the needle valve 206 is unseated from the orifice 190.

While FIGS. 5A, 5B, 6A, and 6B show the orifice 190 as including an enlarged portion 193 and a reduced portion 197, the scope of the disclosure is not so limited. Rather, in some implementations, the orifice 190 may omit the enlarged portion 193. For example, in some implementations, the orifice 190 may form a passage having a uniform cross-sectional shape. In such instances, a valve, such as a needle valve similar to needle valve 206, may include a valve body that extends into an end of the orifice to control fluid flow through the orifice.

In other instances, the valve body may abut a valve seat formed at an end of the orifice to control fluid flow through the orifice. For example, the valve seat may be a portion of an end surface of an insert, which may be similar to insert 192, through which the orifice is formed. The portion of the end surface forming the valve seat may surround the orifice opening formed in the end surface. When the valve body is in contact with the valve seat, fluid flow through the orifice is prevented. When the valve body is displaced from the valve seat, fluid is permitted to flow through the orifice. An orifice and valve body configuration of this type may form an on/off valve such that, when the valve body engages the valve seat, the valve is in an "off" configuration preventing fluid flow. When the valve body is displaced from the valve seat, the valve is in an "on" configuration permitting fluid flow. Further, once the valve is placed in the "on" configuration, the fluid flow rate through the orifice is substantially constant and unchanging notwithstanding the amount by which the valve body is separated from the valve seat.

Continuing with reference to FIGS. 5A, 5B, 6A, and 6B, the plunger 182 is disposed within a cavity 186 formed in the plunger housing 184, and a portion of the plunger housing 184 is received in a cavity 188 formed in the valve body 142. The plunger 182 is slideable within the cavity 186. The orifice 190 is formed within a passage 195 of the plunger housing 184. The passage 195 and the cavity 186 are in fluid communication with each other. The orifice 190 may be formed by an insert 192 that is disposed within the passage 195. As indicated above, the enlarged portion 193 of the orifice 190 is adapted to receive a needle valve 206, which is discussed in more detail below. In some instances, the orifice 190 may have a size of 0.10 mm to 1.0 mm. In other instances, the size of the orifice 190 may be larger or smaller than the indicated range. For example, in some instances, the orifice 190 may have a size of 0.005 mm to 0.05 mm. More generally, the size of the orifice 190 may be any desired size. In other instances, the orifice 190 may be integrally formed within the plunger housing 184, e.g., within the passage 195 of the plunger housing 184.

One or more seals 194 may be disposed between an inner surface 196 of the passage 188 and plunger housing 184. In some instances, the seals 194 may be disposed in annular grooves 198 formed in the proximal end 200 of the plunger housing 184. Similar to seals 164 and 170, described above, the one or more seals 194 may be one or more O-rings or any other desired or suitable sealing device or material adapted to provide a fluid-tight or substantially fluid-tight seal between the plunger housing 184 and the valve body 142.

The plunger 182 may also include a sealing member 202 disposed between an inner surface 204 of the cavity 186 and the plunger 182. The sealing member 202 may be formed from any desired or suitable material and is adapted to provide a fluid-tight or substantially fluid-tight seal between the plunger housing 184 and the plunger 182.

The valve body 142 also includes a needle valve 206 at a proximal end 208 thereof. One or more apertures 210 may be formed in the proximal end 208 of the valve body 142. The one or more apertures 210 provide fluid communication between the cavity 151 and cavity 188. The needle valve 206 extends into the enlarged portion 193 of the orifice 190. When the assembly 161 is in an unactuated position, the needle valve 206 may be seated within the orifice 190, sealing off the cavity 151 from the cavity 186.

In some instances, the needle valve 206 may have a tapered shape. For example, the needle valve 206 may taper from a proximal end 212 to a distal tip 214. In some instances, the enlarged portion 193 of the orifice 190 may have a constant cross-sectional size. However, the scope of the disclosure is not so limited. Rather, in some instances, the needle valve 206 may have a constant cross-sectional shape, and the enlarged portion 193 of the orifice 190 may be flared. In still other instances, the needle valve 206 may have a tapered shape and the enlarged portion 193 of the orifice 190 may be flared. In still other implementations, the needle valve 206 and the enlarged portion 193 of the orifice 190 may have constant cross-sectional shapes. As discussed in more detail below, the needle valve 206 is moveable relative to the orifice 190.

Figure 7:
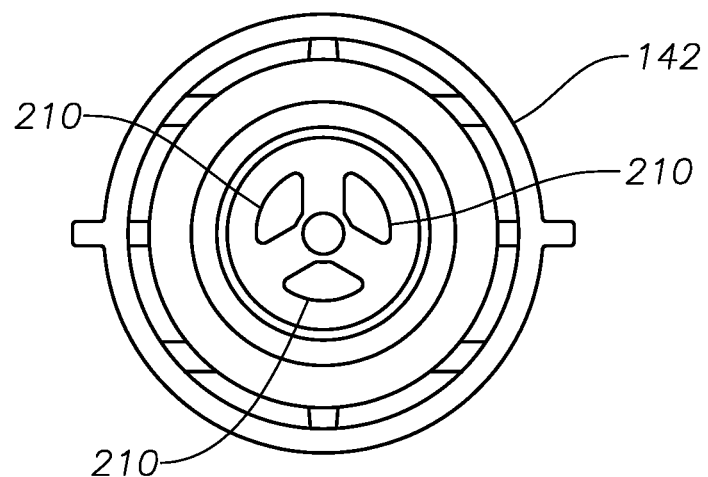
FIG. 7 is a back view of an example valve body.

FIG. 7 shows a proximal end view of the valve body 142. In this example, the valve body 142 includes three apertures 210. However, the valve body 142 may include one, two, or any number of apertures 210.

A fluid may be disposed in the second portion 155 of the cavity 151 between the piston 144 and the valve body 142. In some instances, the fluid may be a substantially incompressible fluid, such as a liquid. Example liquids include an oil (such as a silicone oil), propylene glycol, glycerin, water, saline, or any other substantially incompressible fluid. The seals 164 and 170 retain the fluid between the piston 144 and the valve body 142.

Figure 8:
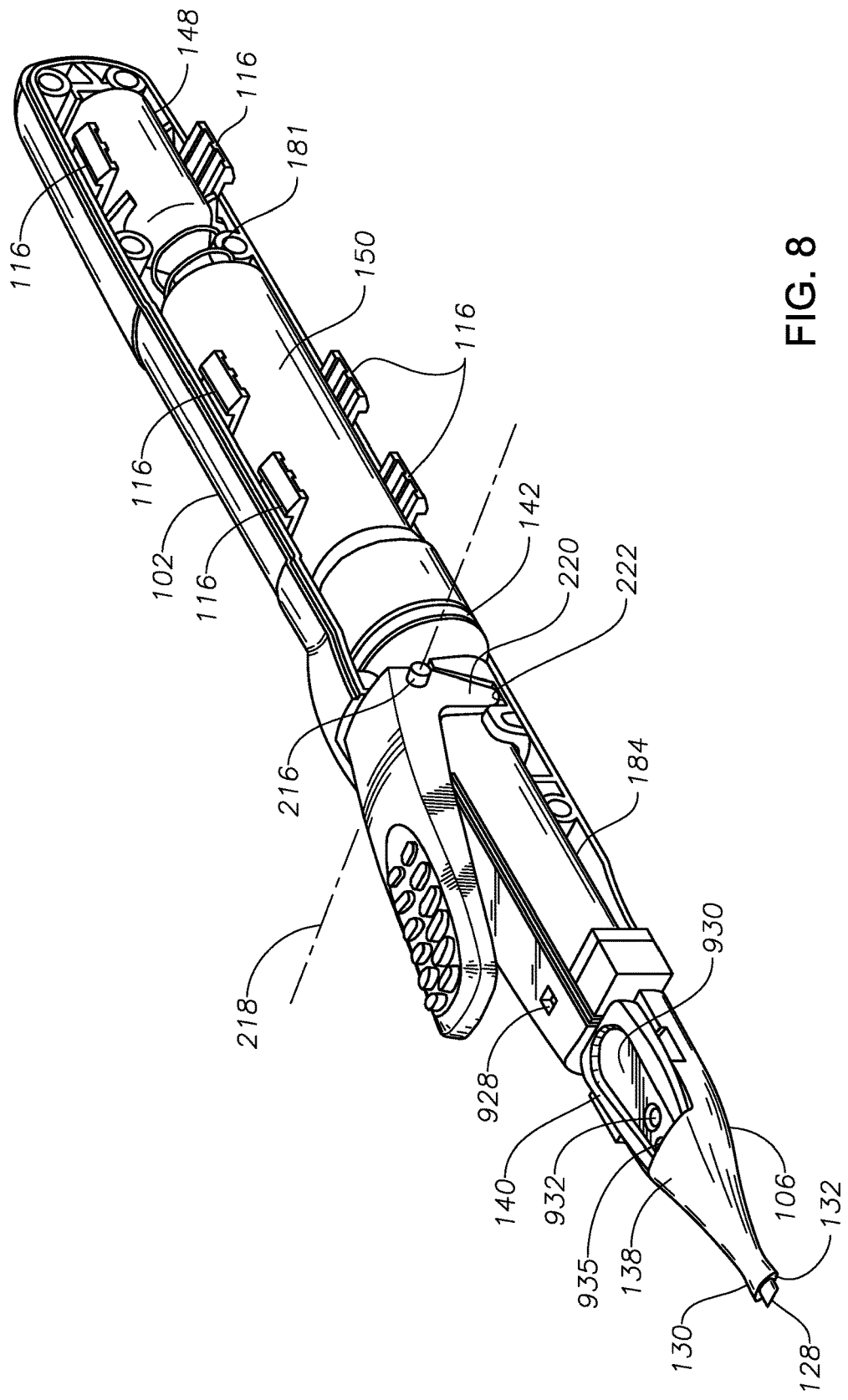
FIG. 8 is a perspective view of an example intraocular lens inserter with a portion of thereof removed.

Referring to FIG. 8, the lever 104 includes protrusions 216. One of the protrusions 216 is shown, while the other is provided on a side of the lever 104 opposite the side shown in FIG. 8. The protrusions 216 may be integrally formed in the lever 104, or, in other instances, the protrusions 216 may be separate components added to the lever 104. Each of the protrusions 216 is received into mating receptacles formed in the body 102. The protrusions 216 and mating receptacles define a pivoting axis 218 of the lever 102. Thus, when the lever is depressed, the lever 104 pivots about this pivoting axis 218.

Figure 11:
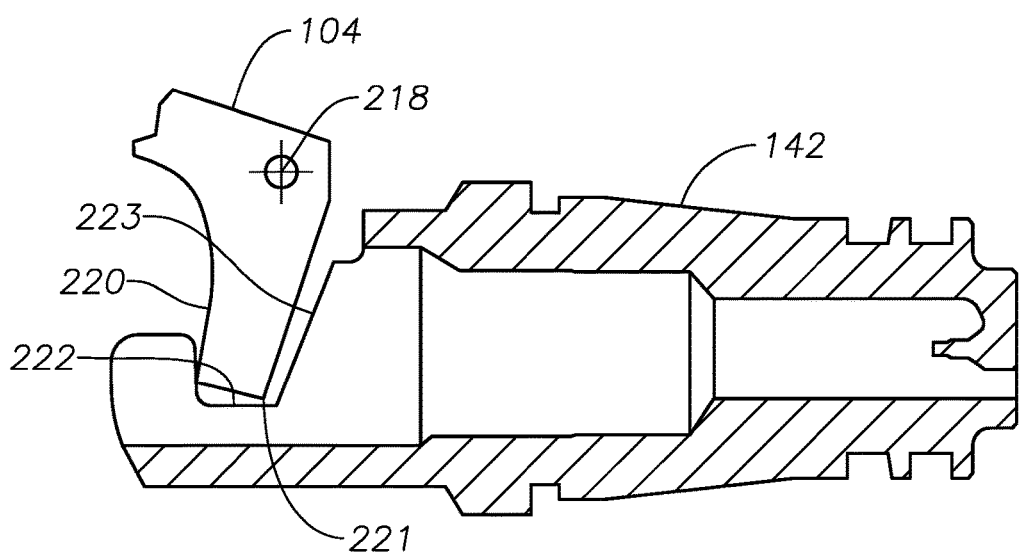
FIG. 11 shows a side detail view of a portion of the lever and valve body.

Referring to FIGS. 8 and 11, the lever 104 includes lever arms or legs 220 that are received into recesses 222 formed in the valve body 142. The legs 220 are operable to displace the valve body 142, piston 144, and bulkhead 146 proximally when the lever 104 is depressed. For example, when the lever 104 is depressed, a corner edge 221 of the leg 220 contacts a surface 223 of the recess 222. As the lever 104 continues to be depressed, the legs 220 swing proximally, resulting in displacement of the valve body 142 (and, consequently, the assembly 161) in the proximal direction.

Figure 6A:
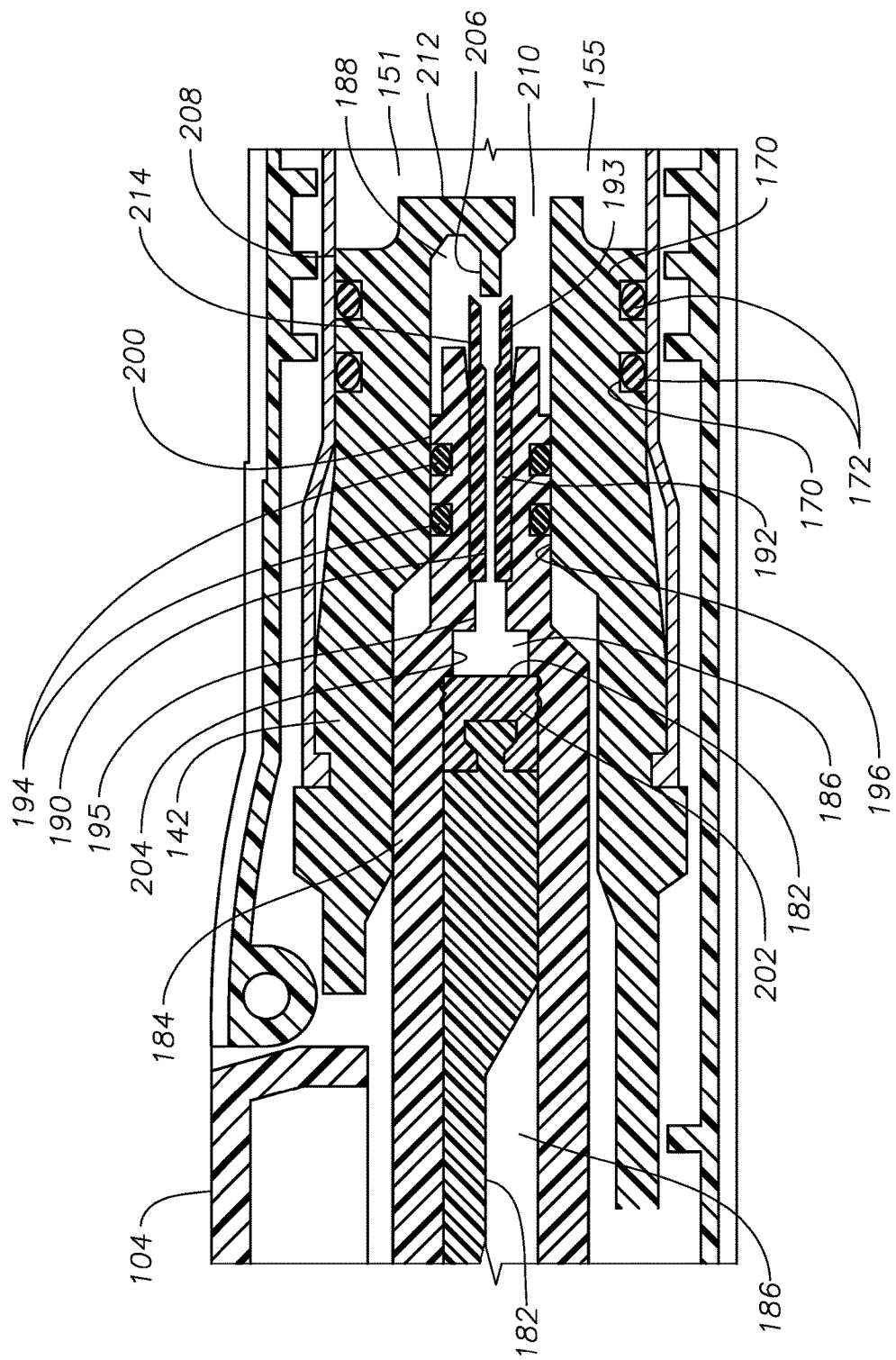
FIGS. 6A and 6B are detail views of the partial cross-sectional view of the example intraocular lens inserter of FIG. 5 with the interior assembly in an articulated position.
Figure 6B:
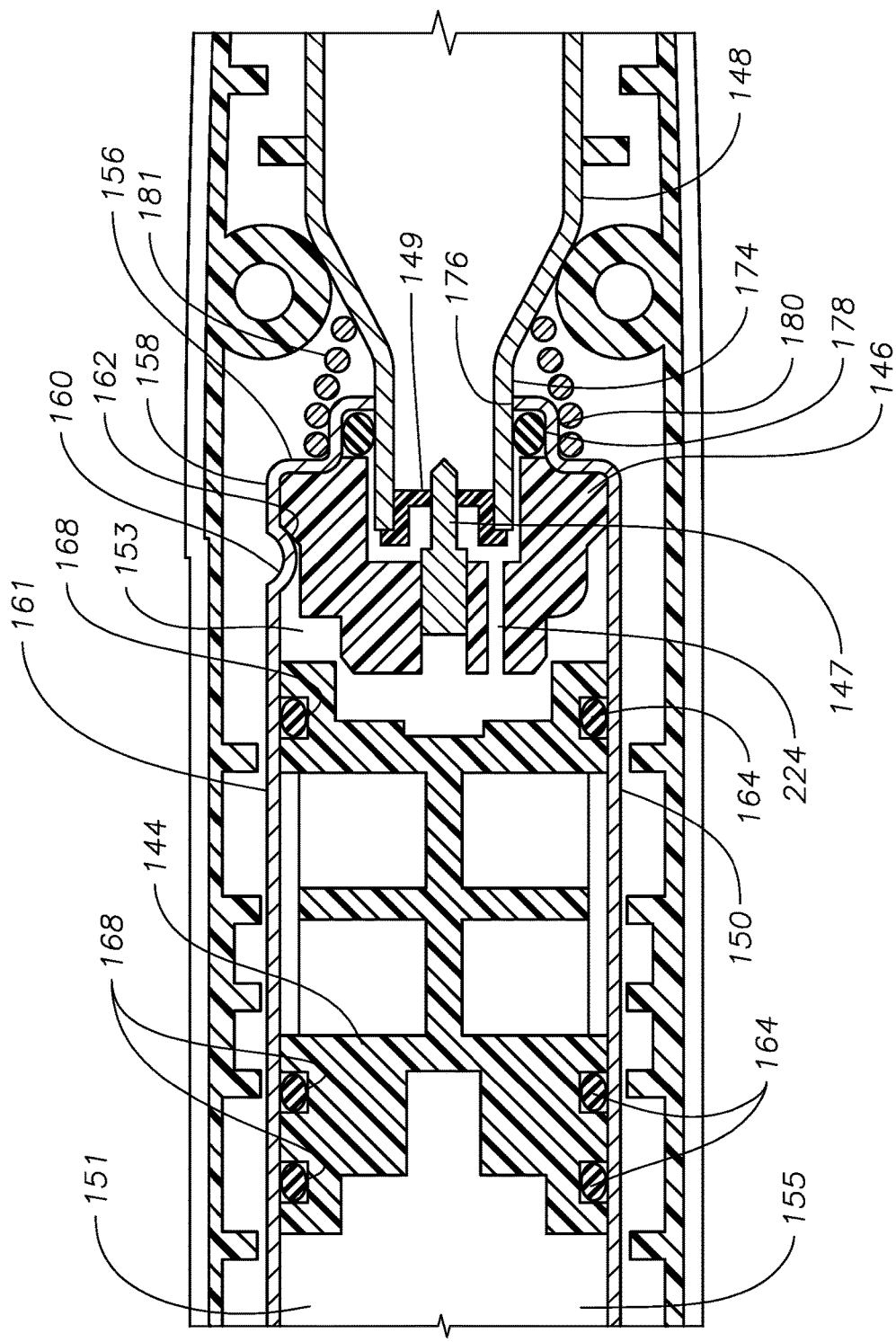

The biasing member 181 may provide a dual function. FIG. 5 shows the inner housing 150 in an unactuated position. The biasing member 181 may provide a biasing force to maintain the inner housing 150 in the unactuated position. This may be desirable during shipping and/or handling of the IOL inserter 100 prior to use. Thus, in this condition, the biasing member 181 aids in preventing unintended operation of the IOL inserter 100. The biasing member 181 also provides a return force during actuation of the IOL inserter 100 and the associated displacement of the inner housing 150, as shown in FIGS. 6A and 6B.

In operation, a user grasps the body 102 of the IOL injector 100 and inserts the distal tip 126 into a wound formed in an eye. In some instances, the distal tip 126 may be advanced through the wound until the end surface 132 of the wound guard 130 contacts an outer surface of the eye. The lever 104 may then be depressed. As explained above, depressing the lever 104 moves the assembly 161 proximally as a result of the interaction between the legs 220 of the lever 104 and the recesses 222 formed in the valve body 142. As the valve body 142, piston 144, inner housing 150, and bulkhead 146 are moved proximally, the piercing member 147 pierces the lid 149 of the canister 148. In addition, the needle valve 206 is moved distally, unseating the needle valve 206 from the orifice 190, such as the enlarged portion 193 of the orifice 190. As a result, fluid communication between cavity 188 and the passage 204 is provided. Additionally, the biasing member 181 is compressed between the inner housing 150 and the canister 148. Thus, as the lever 104 is depressed, the lid 149 of the canister 148 is punctured and the needle valve 206 is unseated simultaneously.

Puncture of the lid 149 releases the compressed gas contained therein. The released gas passes through a passage 224 formed through the bulkhead 146 and impinges upon the proximal end 226 of the piston 144. The gas pressure applied to the piston 144 moves the piston 144 distally within the cavity 151 of the inner housing 150. As mentioned above, in some instances, a portion of the material contained within the canister 148 remains in liquid form. This liquid provides an additional volume of gas to fill a portion of the cavity 151 between the bulkhead 146 and the piston 144 that results as the piston moves distally. The portion of liquid within the canister 148 is available to vaporize and fill this increasing volume, thereby maintaining a substantially constant gas pressure on the piston 144 during operation of the IOL inserter 100.

As the piston 144 travels distally within the inner housing 150, the piston 144 forces the liquid contained within the second portion 155 of the cavity 151 into the orifice 190. The liquid passes through the orifice 190 and impinges upon the proximal end of the plunger 202 and displaces the plunger 202 distally. While the lever 104 remains depressed, the plunger 202 will continue to be displaced distally. As the plunger 202 moves distally, the plunger tip 228 engages the IOL disposed in the chamber 134 and displaces the IOL distally, folding the IOL in the process. As the lever 104 remains depressed, the displacement of the plunger 202 continues, causing the folded IOL to emerge from the opening 128 and, ultimately, to be fully expelled from the IOL inserter 100.

In some instances, the rate at which the plunger 202 may be made to move may be varied by the amount by which the lever 104 is depressed. For example, if a user desires a low rate of advancement, the user may depress the lever 104 only a small amount. If a user desires a larger rate of advancement, the lever 104 may be depress a larger amount. A change in the rate of advancement of the plunger 202 caused by a variation in the amount by which the lever 104 is depressed may be, for example, the result of a tapered shape of the needle valve 206. As the amount by which the needle valve 206 is withdrawn from the enlarged portion 193 of the orifice 190, an annular space formed between the proximal end of the enlarged portion 193 and the needle valve 206 increases due to the tapered shape of the needle valve 206. As this annular space increases, the fluid flow resistance of liquid decreases, thereby resulting in a higher hydraulic flow being exerted against the plunger 202. As a result, the rate of movement of the plunger 202 increases. As the amount by which the needle valve 206 is further withdrawn, the cross sectional area of the annular gap increases to exceed the cross sectional area of the orifice 190, thereby imparting a throttling limit to the flow exerted against the plunger 202. As a result, the rate of movement of the plunger 202 is controlled to an upper limit defined by the orifice 190 and the viscosity of the liquid.

As movement of the plunger 202 continues, such as distal movement through the cavity 186 formed in the plunger housing 184, a distal tip of the plunger 202 contacts an intraocular lens housed within the chamber 134 and displaces the intraocular lens distally within the chamber 134 and lumen 135. As the intraocular lens is advanced by the plunger 202, the intraocular lens is folded and ultimately expelled from the IOL inserter 100 via the opening 128.

The rate at which the plunge 202 may be advanced may be varied by the amount by which the lever 104 is depressed. In some instances, the relationship between the rate at which the plunger 202 is advanced and an amount by which the lever 104 is depressed may be a linear relationship. In other instances, this relationship may be nonlinear. Further, in some instances, when the lever 104 is released, the lever 104 returns to an initial position, such as due to the biasing force provided by the biasing member 181, urging the assembly 161 distally and returning the assembly 161 to its initial position. As a result, the needle valve 206 reseats within the orifice 190, sealing the orifice 190 and preventing the fluid within the second portion 155 of the cavity 151 from acting on the plunger 202. Consequently, advancement of the plunger 202 ceases.

Various aspects of the IOL inserter 100 may affect a speed at which the plunger 202 may be made to advance, and these aspects may be varied in order to establish a desired rate of advancement. Some of these aspects may include the viscosity of liquid contained within the second portion 155 of the cavity 151, a pressure within the canister 148, a size of the orifice 190, an amount by which the needle valve 206 has been withdrawn from the orifice 190, an amount by which the needle valve 206 and/or the enlarged portion 193 of the orifice tapers, and/or a material of the IOL. One or more of these aspects may be varied in order to achieve a desired rate of advancement of the plunger 202.

Figure 9:
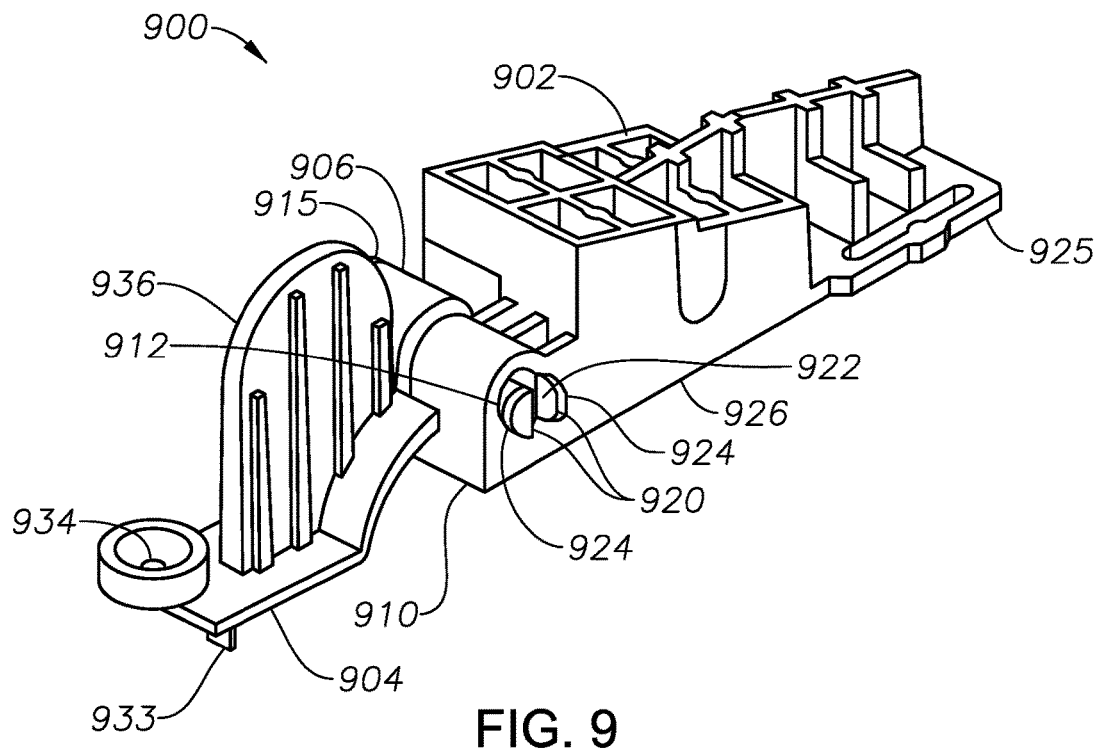
FIG. 9 is a perspective view of an example lever lock.

FIG. 9 shows an example lever lock 900. The lever lock 900 may be coupled to the IOL inserter 100 and a portion of the lever lock 90 may be interposed between the body 102 and the lever 104. The lever lock 900 may be coupled to the IOL inserter 100 prior to use (for example, prior to shipping and during shipping) in order to prevent inadvertent actuation of the lever 104.

The lever lock 900 may include a first portion 902 and a second portion 904. The first portion 902 and the second portion 904 may be connected with hinged connection. A proximal end 908 of the second portion 904 may form a bore therethrough, and a distal end 910 of the first portion 902 may also define a bore. The bore defined by the proximal end 906 of the second portion 904 may align with the bore defined formed in the distal end 910 of the first portion 902 to define a passage 912. A hinge pin 914 may be received into the passage 912. In some instances, a first end of the hinge pin 914 may have a flanged portion 915 that is larger than a size of the passage 912. A second end of the hinge pin 914 may include flexible members 920 separated by a gap 922. The flexible members 920 include an enlarged portion 924 at their respective ends.

The hinge pin 914 may be received into the passage 912. As the flexible members 920 are passed through the passage 912, the flexible members 920 may flex towards each other. When the flexible members 920 exits the passage 912, the flexible members 920 return to their at-rest position, causing retention of the hinge pin 914 within the passage 912. The flanged portion 915 and the enlarged portions 924 cooperate to keep the hinge pin 914 retained within the passage 912 and the first and second portions 902, 904 pivotably connected.

Figure 10:
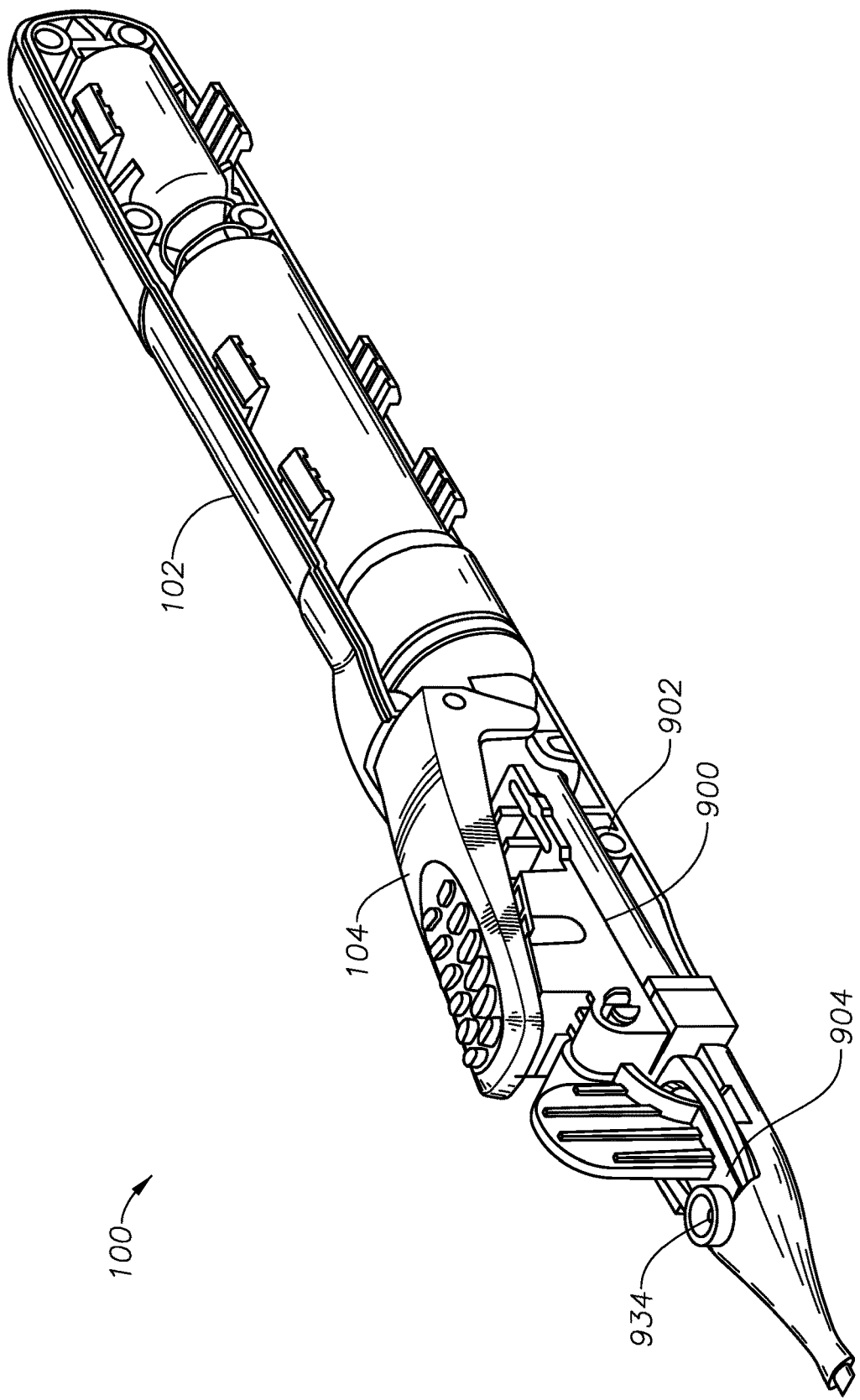
FIG. 10 is a perspective view of an example intraocular lens inserter with a lever lock installed thereonto.

As shown in FIGS. 8 and 10, the first portion 902 may be interposed between the body 102 and the lever 104, preventing depression of the lever 104. One or more protrusions protruding from surface 926 may be received into corresponding receptacles 928 formed in the body 102. In some implementations, the first portion 902 may include additional protrusions located proximate to the proximal end of body 102 are may be received into corresponding openings formed in body 102. The second portion 904 may be received into a recess 930 formed in the door 140. A first aperture 932 may also be formed into the door 140. The first aperture 932 provides fluid communication between the exterior of the IOL inserter 100 and the chamber 134. A protrusion 933 formed on the second portion 904 of the lever lock 900 is received into the first aperture 932. The protrusion 933 acts as a barrier that prevents advancement of the IOL within the chamber 134. In some instances, the protrusion 933 may reside between a distal haptic and an optic of the IOL.

A second aperture 935 may also be formed in the door 140. The aperture 935 may be utilized to introduce a lubricant (such as a viscoelastic material) to reduce friction between the nozzle 106 as an intraocular lens is pushed through the lumen 135. As shown in FIGS. 9-10, the second portion 904 of the lever lock 900 may include an aperture 934 that aligns with the aperture 932 when the second portion 904 is properly seated in the recess 930. This permits introduction of a lubricant into the chamber 134 while the lever lock 900 remains coupled to the body 102.

A user, such as a physician or other medical professional, may remove the lever lock 900 by grasping a protrusion 936 and pivoting the second portion 902 about the hinge pin 914 away from the body 102 so as to unseat the second portion 902 from the recess 930 and remove the protrusion 933 from the aperture 932. The user may then pull the second portion 902 distally to remove the first portion 902 and, consequently, the entire lever lock 900 from the IOL inserter 100. In some instances, the lever lock 900 may be discarded thereafter.

Although the disclosure provides numerous examples, the scope of the present disclosure is not so limited. Rather, a wide range of modification, change, and substitution is contemplated in the foregoing disclosure. It is understood that such variations may be made to the foregoing without departing from the scope of the present disclosure.

What is claimed is:

1. An intraocular lens inserter comprising:
an inserter body defining a first interior cavity;
a compressed gas container coupled to the inserter body;
an assembly disposed within the first interior cavity and moveable within the first interior cavity relative to the inserter body, the assembly comprising:
a housing;
a second interior cavity formed within the housing; and
a moveable member disposed within the second interior cavity and moveable therein relative to the housing, the moveable member dividing the second interior cavity into a first portion adapted to receive a compressed gas from the compressed gas container and a second portion configured to contain a substantially incompressible fluid, the moveable member configured to impart a pressure from the compressed gas to the substantially incompressible fluid; and
a plunger, the plunger movable in response to pressure imparted by the substantially incompressible fluid.

2. The intraocular lens inserter of claim 1, further comprising an actuator moveable between an unactuated position and an actuated position, the actuator operable to displace the assembly between an initial position and a displaced position relative to the compressed gas container in response to movement of the actuator to the actuated position.

3. The intraocular lens inserter of claim 2, further comprising a resilient member disposed between the housing and the compressed gas container, the resilient member configured to apply a biasing force that urges the assembly towards the initial position when the actuator is moved into the actuated position.

4. The intraocular lens inserter of claim 1, wherein the assembly further comprises a piercing member configured to pierce the compressed gas container.

5. The intraocular lens inserter of claim 4, wherein the piercing member is configured to pierce the compressed gas container in response to displacement of the assembly relative to the compressed gas container.

6. The intraocular lens inserter of claim 1, further comprising an orifice, wherein the assembly further comprises a valve body comprising:
an aperture; and
a needle valve receivable into the orifice.

7. The intraocular lens inserter of claim 6, wherein displacement of the assembly within the inserter body displaces the needle valve relative to the orifice resulting in fluid communication between the second portion of the second interior cavity and the orifice via the aperture.

8. The intraocular lens inserter of claim 7, further comprising a plunger housing, the plunger housing forming a third interior cavity configured to receive the plunger, wherein the third interior cavity is in fluid communication with the orifice, and wherein the substantially incompressible fluid is flowable through the aperture and the orifice to apply pressure to the plunger to displace the plunger within the third interior cavity in response to displacement of the assembly within the inserter body.

9. The intraocular lens inserter of claim 6, wherein the needle valve comprises a tapered surface, and wherein displacement of the needle valve within the orifice forms a gap between the tapered surface of the needle valve and the orifice that varies with an amount by which the needle valve is moved relative to the orifice.

10. An intraocular lens inserter comprising:
an inserter body defining a first interior cavity;
a pressurized gas canister disposed in the first interior cavity;
an assembly disposed in the first interior cavity and moveable therein relative to the inserter body, the assembly comprising:
a first housing defining a second interior cavity;
a valve body disposed at a first end of the first housing;
a moveable member disposed in the second interior cavity and movable relative to the first housing; and
a piercing member disposed at a second end of the first housing, opposite the first end;
an actuator pivotably coupled to the inserter body, the actuator comprising a lever arm that engages the assembly, the actuator operable to displace the assembly within the inserter body when the actuator is pivoted relative to the inserter body.

11. The intraocular lens inserter of claim 10, wherein the piercing member is configured to pierce the pressurized gas canister when the assembly is displaced within the inserter body.

12. The intraocular lens inserter of claim 11, wherein the assembly further comprises a passage operable to communicate pressurized gas released from the pressurized gas canister into the second interior cavity.

13. The intraocular lens inserter of claim 10, wherein the moveable member is displaceable within the second interior cavity in response to pressurized gas released from the pressurized gas canister.

14. The intraocular lens inserter of claim 13, wherein the assembly further comprises a passage between the first portion and the pressurized gas canister, and wherein pressurized gas released from the pressurized gas canister is communicated to the first portion via the passage.

15. The intraocular lens inserter of claim 10, wherein the moveable member divides the second interior cavity into a first portion and a second portion, and wherein a substantially incompressible fluid is disposed in the second portion.

16. The intraocular lens inserter of claim 15, further comprising:
a plunger housing;
a plunger received into a chamber formed in the plunger housing; and
an orifice formed in the plunger housing, the orifice in fluid communication with the chamber formed in the plunger housing;
wherein the valve body comprises a needle valve removably received into the orifice, the needle valve displaceable from the orifice in response to a displacement of the assembly within the inserter body, wherein displacement of the needle valve from the orifice provides fluid communication between a substantially incompressible fluid contained within the second portion of the second interior cavity and the chamber formed in the plunger housing.

17. The intraocular lens inserter of claim 16, wherein the assembly is moveable between a first position in which the needle valve is seated within the orifice and a second position in which the needle valve is unseated from the orifice and the piercing member penetrates the pressurized gas container canister to release the pressurized gas into the first portion in response to articulation of the actuator from a third position to a fourth position.

18. The intraocular lens inserter of claim 17, wherein the movable member is displaceable within the second interior cavity and operable to transmit the pressure of the pressurized gas within the first portion to the substantially incompressible fluid contained in the second portion in response to the pressure of the pressurized gas,
wherein the substantially incompressible fluid is flowable into the chamber via the orifice in response to displacement of the moveable member, and
wherein the plunger is movable within the chamber in response to pressure transmitted thereto by the substantially incompressible fluid.

19. The intraocular lens inserter of claim 17, further comprising a biasing member disposed between the assembly and the pressurized gas canister, and wherein the biasing member applies a biasing force when the assembly is displaced from the first position that urges the assembly back into the first position.

20. The intraocular lens inserter of claim 16, wherein the needle valve comprises a tapered surface, wherein a gap is formed between the tapered surface of the needle valve and the orifice when the needle valve is unseated from the orifice, and wherein a size of the gap is altered by the amount by which the needle valve is displaced relative to the orifice.

21. The intraocular lens inserter of claim 20, wherein the size of the gap is altered in response to an amount by which the actuator is pivoted relative to the inserter body.

* * * * *